US011753362B2

(12) United States Patent
Yan et al.

(10) Patent No.: US 11,753,362 B2
(45) Date of Patent: Sep. 12, 2023

(54) METHOD OF OXIDIZING GLYCOLALDEHYDE USING NITRIC ACID

(71) Applicant: RHODIA OPERATIONS, Aubervilliers (FR)

(72) Inventors: Zhen Yan, Taiyuan (CN); Bright Kusema, Shanghai (CN); Sergio Mastroianni, Lyons (FR); Stéphane Streiff, Shanghai (CN); Philippe Marion, Vernaison (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 17/612,088

(22) PCT Filed: Jun. 4, 2019

(86) PCT No.: PCT/CN2019/089998
§ 371 (c)(1),
(2) Date: Nov. 17, 2021

(87) PCT Pub. No.: WO2020/243907
PCT Pub. Date: Dec. 10, 2020

(65) Prior Publication Data
US 2022/0213018 A1 Jul. 7, 2022

(51) Int. Cl.
*C07C 51/27* (2006.01)
(52) U.S. Cl.
CPC .................................. *C07C 51/27* (2013.01)
(58) Field of Classification Search
CPC ..................................................... C07C 51/27
See application file for complete search history.

(56) References Cited

U.S. PATENT DOCUMENTS

| | | | |
|---|---|---|---|
| 4,698,441 A | 10/1987 | Mitani et al. | |
| 5,397,582 A | 3/1995 | Underwood et al. | |
| 7,094,932 B2 | 8/2006 | Majerski et al. | |
| 8,754,255 B2 | 6/2014 | Bleger et al. | |
| 9,187,398 B2 * | 11/2015 | Donen | C07C 51/316 |
| 2013/0281733 A1 | 10/2013 | Han et al. | |

FOREIGN PATENT DOCUMENTS

| | | |
|---|---|---|
| CN | 105189433 A | 12/2015 |
| CN | 105669424 A | 6/2016 |
| JP | H07309803 A | 11/1995 |
| JP | 2001019657 A | 1/2001 |
| WO | 2017216311 A1 | 12/2017 |
| WO | 2018095973 A1 | 5/2018 |

OTHER PUBLICATIONS

Zang Zhiyong, Reaction and separation process for research of gloxal produced with acetaldehyde, Chinese doctorial dissortations full-text database engineering science and technology I, vol. 2013,No. 5, (Year: 2013).*
Andronov L.M. et al., Mechanism of the oxidation of glyceraldehyde by molecular oxygen, Institute of chemical physics, Academy of science of the USSO, No. 3, pp. 519-524 (Year: 1967).*
Shibata. et. al., Selective oxidation of the aldehyde functional group in the glycolaldehyde molecule at Pt electrodes modified by Sb ad-atoms, Journal of Electroanalytical Chemistry (1993), 344(1-2), 389-93.
Shibata. et. al., Selective oxidation of the aldehyde functional group in the glycolaldehyde molecule at Pt electrodes modified by ad-atoms, Electrochimica Acta (1994), 39(11-12), 1877-80.
Perri. et. al., Secondary organic aerosol production from aqueous photooxidation of glycolaldehyde: Laboratory experiments, Atmospheric Environment (2009), 43(8), 1487-1497.
Thomas. et. al., Real-Time Studies of Iron Oxalate-Mediated Oxidation of Glycolaldehyde as a Model for Photochemical Aging of Aqueous Tropospheric Aerosols, Environmental Science & Technology (2016), 50(22), 12241-12249.
Andronov. et. al., Mechanism of glyceraldehyde oxidation by molecular oxygen, Izvestiya Akademii Nauk SSSR, Seriya Khimicheskaya (1967), (3), 519-24.
Andronov. et. al., Mechanism of the Oxidation of Glyceraldehyde by Molecular Oxygen, Bulletin of the Academy of Sciences of the USSR, Division of chemical science vol. 16, pp. 504-508 (1967) English counterpart of Andronov. et. al.
Svetklov. et. al., Oxidation of Diethylene Glycol with Nitric Acid, Russian Journal of Organic Chemistry (Translation of Zhurnal Organicheskoi Khimii) (2002), 38(5), 753.
Zhang. et. al., Reaction and Separation Process Research of Glyoxal Produced with Acetaldehyde, Chinese Doctoral Dissertations Full-Text Database, Jun. 1, 2013 (Jun. 1, 2013), pp. 1-125 English Abstract in Zhang_2013 pdf.

* cited by examiner

*Primary Examiner* — Yate' K Cutliff
(74) *Attorney, Agent, or Firm* — Osha Bergman Watanabe & Burton LLP

(57) ABSTRACT

The present invention relates to a method of synthesizing at least one organic acid comprising oxidizing glycolaldehyde with nitric acid in the presence of a solvent. Advantageously, it is an industrially applicable process, which prepares organic acid, notably glycolic acid and/or glyoxylic acid in a high yield based on bio-based feedstocks.

14 Claims, No Drawings

METHOD OF OXIDIZING GLYCOLALDEHYDE USING NITRIC ACID

This application is a U.S. national phase entry under 35 U.S.C. § 371 of International Application No. PCT/CN2019/089998, filed on Jun. 4, 2019, the entire content of which is explicitly incorporated herein by this reference.

TECHNICAL FIELD

The present invention relates to a method of synthesizing at least one organic acid comprising oxidizing glycolaldehyde with nitric acid in the presence of a solvent.

BACKGROUND

Glycolic acid has conventionally been used mainly as boiler compounds, cleaning agents, leather tanning agents, chelating agents of metal ions and the like. In recent years, its applications have expanded to cosmetics, personal care and pharmaceuticals for external use. Glycolic acid to be used for pharmaceuticals requires high purity grade and is desired to contain a lower level of harmful impurities. Glycolic acid has recently been expected also as a raw material for polyglycolic acid having biodegradability and a gas barrier function.

Typical examples of a conventionally known method for producing glycolic acid include (1) a method of reacting carbon monoxide, formaldehyde and water in the presence of a strongly acidic catalyst under high-temperature and high-pressure conditions, (2) a method of reacting formaldehyde with hydrogen cyanide, (3) a method of reacting chloroacetic acid with sodium hydroxide, (4) a method of carrying out a Cannizzaro reaction between glyoxal available by oxidation of ethylene glycol and a strong alkali to form a glycolate salt, and then adding an acid to liberate glycolic acid from the resulting glycolate salt; (5) a method of carrying out a liquid-phase reaction between glyoxal available by oxidation of ethylene glycol and water in the presence of an inorganic catalyst; (6) a method for catalytic oxidation of ethylene glycol in the presence of a noble metal catalyst and oxygen; and (7) a method of carrying out oxidative esterification of ethylene glycol with methanol and oxygen to obtain methyl glycolate and then hydrolyzing into glycolic acid.

The method (1) is performed in the presence of a strongly acidic catalyst such as acidic polyoxometalate under high-temperature and high-pressure conditions. Thus, special reaction equipment and special reaction conditions of high temperature and high pressure are necessary. At the same time, glycolic acid obtained using reaction conditions of high temperature and high pressure contains a large amount of various impurities.

The method (2) of reacting formaldehyde with hydrogen cyanide requires the use of an extremely poisonous starting raw material, i.e., hydrogen cyanide.

The method (3) of reacting monochloroacetic acid with sodium hydroxide requires use of an about stoichiometric amount of sodium hydroxide. One problem is that sodium chloride generated raises the slurry concentration, leading to poor operability. Another problem is that this salt cannot be removed completely and remains in the product.

A problem common to the methods (4) to (7) is that ethylene glycol is produced from fossil-based feedstocks. For example, ethylene glycol can be produced using ethylene oxide as a raw material. The step of producing ethylene glycol is long and in addition, ethylene oxide, which is explosive, must be well handled in the production process.

As reported by Electrochimica Acta (1994), 39(11-12), 1877-80, previous efforts to oxidize glycolaldehyde have shown that the primary product from the electrochemical oxidation of glycolaldehyde over Pt electrodes is glyoxal, with only minor production of glycolic acid. Electrochemical modification of the electrode surface by deposition of an ad-atom layer of Bi was necessary to shift the selectivity to glycolic acid; a process which is not easily translated into industrial production.

Glyoxylic acid is a key intermediate for agrochemicals, aromas, cosmetics, pharmaceuticals and polymers. The main application for glyoxylic acid is vanillin for food, beverages and fragrances. Glyoxylic acid is also used for water purification, pesticides and as an intermediate for varnish materials and dyes. It can also be used in the preservation of food, as a crosslinking agent of polymerization and as a plating additive.

Conventionally known commercial method for producing glyoxylic acid is by the oxidation of glyoxal. For example, U.S. Pat. No. 4,698,441 discloses that nitric acid oxidation of glyoxal was used as an industrial process for producing glyoxylic acid. Disadvantageously, glyoxal is a fossil-based raw material and oxalic acid is formed as a byproduct in this process.

Glyoxylic acid can also be produced by ozonation of maleic acid. The main disadvantage of this process is that ozone and peroxide containing ozonolysis products are unsafe and prone to explosions.

The conventional production methods have the above-described drawbacks. In particular, glycolic acid or glyoxylic acid obtained by these methods utilize fossil-based feedstocks.

There is still a need to develop an industrially applicable process to prepare organic acids, notably glycolic acid and/or glyoxylic acid with a high yield and selectivity based on inexpensive and sustainable feedstocks, such as bio-based materials with desired characteristics such as low cost, simple equipment, mild reaction conditions, ease of handle, which can overcome the drawbacks in prior arts.

SUMMARY OF THE INVENTION

The present invention therefore pertains to a method of synthesizing at least one organic acid comprising oxidizing glycolaldehyde with nitric acid in the presence of a solvent.

The invention also concerns a mixture comprising glycolaldehyde, nitric acid and a solvent.

Definitions

Throughout the description, including the claims, the term "comprising one" should be understood as being synonymous with the term "comprising at least one", unless otherwise specified, and "between" should be understood as being inclusive of the limits.

As used herein, the terminology "($C_n$-$C_m$)" in reference to an organic group, wherein n and m are each integers, indicates that the group may contain from n carbon atoms to m carbon atoms per group.

The articles "a", "an" and "the" are used to refer to one or to more than one (i.e., to at least one) of the grammatical object of the article.

The term "and/or" includes the meanings "and", "or" and also all the other possible combinations of the elements connected to this term.

It is specified that, in the continuation of the description, unless otherwise indicated, the values at the limits are included in the ranges of values which are given.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

Details of the Invention

Glycolaldehyde subject to nitric acid oxidation can be a bio-based raw material. Bio-based raw material refers to a product consisting of a substance, or substances, originally derived from living organisms. These substances may be natural or synthesized organic compounds that exist in nature.

For example, it is known that glycolaldehyde can be produced by high-temperature fragmentation of carbohydrates to produce a mixture of $C_1$-$C_3$ oxygenates such as described in U.S. Pat. Nos. 7,094,932, 5,397,582 and WO 2017/216311.

The carbohydrate used for thermal fragmentation to provide a $C_1$-$C_3$ oxygenate mixture may be mono- and/or disaccharide. In an embodiment, the mono- and/or di-saccharide is selected from the group consisting of sucrose, lactose, xylose, arabinose, ribose, mannose, tagatose, galactose, glucose and fructose; or mixtures thereof. In a further embodiment, the monosaccharide is selected from the group consisting of glucose, galactose, tagatose, mannose, fructose, xylose, arabinose, ribose; or mixtures thereof.

The method according to the present invention can be described as an oxidation process wherein nitric acid serves as the direct source of the actual oxidizing species.

Preferably, glycolaldehyde is oxidized with nitric acid in the presence of an initiator. Advantageously, the initiator does not only help to initiate the oxidation reaction, but also improves the yield of desired organic acid(s).

The initiator is preferably a nitrite, a nitrogen oxide or a mixture thereof. More preferably, the initiator is a nitrite.

The nitrogen oxide is advantageously selected from the group consisting of NO, $NO_2$ and $N_2O_3$.

The nitrite can be an organic compound, namely a nitrite ester; among nitrite esters, alkyl nitrites such as isoamyl nitrite can be cited. The nitrite can also be an inorganic compound, namely a nitrite salt. The nitrite is preferably a nitrite salt. More preferably, the nitrite is ammonium nitrite, an alkali metal nitrite or a mixture thereof. Among alkali metal nitrites, sodium nitrite, potassium nitrite, lithium nitrite and mixtures thereof are especially suitable.

Mineral acid such as hydrochloric acid or sulfuric acid can be used in oxidation reaction with nitric acid to improve the yield of the desired organic acid(s).

The solvent used in the process according to the present invention can be water, ether, methanol or ethanol. Preferable solvent is water.

The organic acid formed by nitric acid oxidation of glycolaldehyde is notably glycolic acid, glyoxylic acid or their mixture.

The method according to the present invention comprises the following steps:

(i) Mixing glycolaldehyde, nitric acid, a solvent and optionally an initiator;

(ii) Heating the mixture obtained at step (i) at proper temperature for proper time to synthesize the desired organic acid.

In some embodiments, a mineral acid above mentioned is introduced into the mixture of step (i).

The skilled person will select the proper temperature and proper time to synthesize the desired organic acid.

In one embodiment, the organic acid is or comprises glycolic acid and glycolaldehyde is oxidized into glycolic acid according to reaction Scheme 1:

Scheme 1

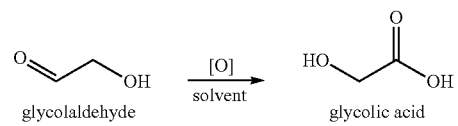

It was found that glycolic acid can be obtained at a high selectivity of at least 70% and a high yield of at least 70% when the concentration of nitric acid is higher than 20 wt. %, preferably higher than 30 wt. % and more preferably from 30 wt. % to 60 wt. %.

The concentration of nitric acid according to the present invention is determined by the way of dividing the weight of nitric acid by the weight of commercial nitric acid and solvent supplied.

For example, the concentration of commercial nitric acid is about 65%. The concentration of nitric acid is calculated as:

$$C_{nitric\,acid}\% = \frac{\text{weight of commercial nitric acid} \times 65\%}{\text{weight of commercial nitric acid} + \text{weight of solvent}} \times 100\%$$

The molar ratio of nitric acid to glycolaldehyde is from 0.5 to 8 mol/mol.

The reaction temperature in this embodiment is from 20 to 120° C.

The reaction time in this embodiment is from 0.25 to 25 h.

Preferably, the reaction is performed in the presence of an initiator. The molar ratio of the initiator to glycolaldehyde is from 0.01 to 0.2 mol/mol and preferably from 0.05 to 0.1 mol/mol.

In another embodiment, the organic acid is or comprises glyoxylic acid and glycolaldehyde is oxidized into glyoxylic acid according to reaction Scheme 2:

Scheme 2

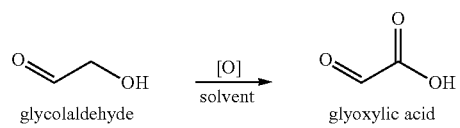

It was found that glyoxylic acid can be obtained at a selectivity of at least 45% and a yield of at least 20%, preferably at least 40% and more preferably at least 50% when the concentration of nitric acid is equal to or lower than 30 wt. %, preferably from 5 wt. % to 30 wt. % and more preferably from 10 wt. % to 20 wt. %.

The molar ratio of nitric acid to glycolaldehyde is from 0.5 to 8 mol/mol.

The reaction temperature in this embodiment is from 20 to 120° C.

The reaction time in this embodiment is from 0.25 h to 25 h.

Preferably, the reaction is performed in the presence of an initiator. The molar ratio of the initiator to glycolaldehyde is from 0.01 to 0.2 mol/mol and preferably from 0.05 to 0.1 mol/mol.

It was surprisingly found that it is the hydroxyl group of glycolaldehyde, instead of the carbonyl group of glycolaldehyde, is directly oxidized to the carboxyl group. The selectivity of glyoxylic acid is stable even when the reaction time is long enough to achieve almost full conversion of glycolaldehyde.

The invention also concerns a mixture comprising glycolaldehyde, nitric acid and a solvent. The solvent has the same meaning as above mentioned.

The mixture comprising glycolaldehyde and nitric acid further comprise an initiator. The initiator has the same meaning as above mentioned.

The following examples are included to illustrate embodiments of the invention. Needless to say, the invention is not limited to described examples.

Experimental Part

Materials

Glycolaldehyde Dimer, CAS No. 23147-58-2, purity >95% from Adamas-beta

Sodium nitrite, CAS No. 7632-0-0, purity AR, >99.0% from Sinopharm

Nitric acid, CAS No. 7697-37-2, purity AR 65-68% from Sinopharm

EXAMPLE 1

240 mg of glycolaldehyde, 28 mg of sodium nitrite, 0.8 g of 65% nitric acid and 2.6 mL of water were mixed in a glass flask with a condenser and heated at 60° C. for 8 hours. After cooling down to room temperature, the products were analyzed with HPLC. The conversion of glycolaldehyde was 92% and the yield to glyoxylic acid was 45%. The other products were glyoxal (9%), glycolic acid (7%) and formic acid (17%).

EXAMPLE 2

480 mg of glycolaldehyde, 56 mg of sodium nitrite, 0.5 g of 65% nitric acid and 1.0 mL of water were mixed in a glass flask with a condenser and heated at 60° C. for 1 hour. After cooling down to room temperature, the products were analyzed with HPLC. The conversion of glycolaldehyde was 30% and the yield to glyoxylic acid was 22%. The other products were glyoxal (3%), glycolic acid (1%), oxalic acid (3%) and formic acid (1%).

EXAMPLE 3

240 mg of glycolaldehyde, 28 mg of sodium nitrite, 1.6 g of 65% nitric acid and 10 mL of water were mixed in a glass flask with a condenser and heated at 60° C. for 24 hours. After cooling down to room temperature, the products were analyzed with HPLC. The conversion of glycolaldehyde was 99% and the yield to glyoxylic acid was 55%. The other products were glyoxal (16%), glycolic acid (5%) and formic acid (17%).

EXAMPLE 4

240 mg of glycolaldehyde, 28 mg of sodium nitrite, 0.4 g of 65% nitric acid and 1.3 mL of water were mixed in a glass flask with a condenser and heated at 40° C. for 24 hours. After cooling down to room temperature, the products were analyzed with HPLC. The conversion of glycolaldehyde was 55% and the yield to glyoxylic acid was 22%. The other products were glyoxal (2%), glycolic acid (5%) and formic acid (11%)

EXAMPLE 5

240 mg of glycolaldehyde, 0.4 g of 65% nitric acid and 0.5 mL of water were mixed in a glass flask with a condenser and heated at 80° C. for 2 hours. After cooling down to room temperature, the products were analyzed with HPLC. The conversion of glycolaldehyde was 100%. The yield to glycolic acid was 78% and the yield of glyoxylic acid was 7%.

EXAMPLE 6

480 mg of glycolaldehyde, 1.0 g of 65% nitric acid and 1.0 mL of water were mixed in a glass flask with a condenser and heated at 60° C. for 2 hours. After cooling down to room temperature, the products were analyzed with HPLC. The conversion of glycolaldehyde was 100%. The yield to glycolic acid was 87% and the yield of glyoxylic acid was 10%.

EXAMPLE 7

480 mg of glycolaldehyde, 60 mg of sodium nitrite, 1.0 g of 65% nitric acid and 1.0 mL of water were mixed in a glass flask with a condenser and heated at 60° C. for 2 hours. After cooling down to room temperature, the products were analyzed with HPLC. The conversion of glycolaldehyde was 100% and the yield to glycolic acid was 92%.

EXAMPLE 8

480 mg of glycolaldehyde, 60 mg of sodium nitrite, 1.0 g of 65% nitric acid and 1.0 mL of water were mixed in a glass flask with a condenser and heated at 60° C. for 15 min. After cooling down to room temperature, the products were analyzed with HPLC. The conversion of glycolaldehyde was 100% and the yield to glycolic acid was 97%.

EXAMPLE 9

312 mg of glycolic acid, 30 mg of sodium nitrite, 1.2 g of 65% nitric acid and 1.0 mL of water were mixed in a glass flask with a condenser and heated at 60° C. for 1 hour. After cooling down to room temperature, the products were analyzed with HPLC. No reaction of glycolic acid was observed.

EXAMPLE 10

256 mg of glycolic acid, 30 mg of sodium nitrite, 0.8 g of 65% nitric acid and 2.6 mL of water were mixed in a glass flask with a condenser and heated at 60° C. for 8 hours. After cooling down to room temperature, the products were analyzed with HPLC. No reaction of glycolic acid was observed.

As shown by Scheme 1, it is clear that only the aldehyde group of glycolaldehyde is oxidized to carboxyl group. However, according to Examples 8 & 9, the hydroxyl group of glycolic acid was not subject to further oxidation in reaction medium having both high and low nitric acid concentration. At least 2 nitric acid concentrations were tested, high nitric acid concentration of 35%, and low nitric acid concentration 15%. Therefore, it can be proved that the hydroxyl group of glycolaldehyde is directly oxidized to carboxyl group in the reaction exemplified by Scheme 2.

The invention claimed is:

1. A method of synthesizing at least one organic acid comprising oxidizing glycolaldehyde with nitric acid in the presence of a solvent, selected from the list consisting of water, ether, methanol and ethanol, and wherein the organic acid is glycolic acid, glyoxylic acid or a mixture thereof.

2. The method according to claim 1, wherein glycolaldehyde is oxidized with nitric acid in the presence of an initiator.

3. The method according to claim 2, wherein the initiator is a nitrite salt.

4. The method according to claim 3, wherein the initiator nitrite salt is selected from the group consisting of ammonium nitrite, sodium nitrite, potassium nitrite, lithium nitrite or a mixture thereof.

5. The method according to any one of claim 1, wherein the organic acid is or comprises glycolic acid and glycolaldehyde is oxidized into glycolic acid according to reaction Scheme 1:

Scheme 1

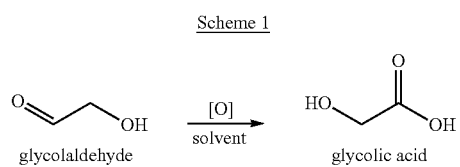

wherein the concentration of nitric acid in the solvent is higher than 20 wt. %.

6. The method according to claim 5, wherein the selectivity to glycolic acid is of at least 70% and the yield to glycolic acid is of at least 70%.

7. The method according to claim 5, wherein the concentration of nitric acid in the solvent is from 30 wt. % to 60 wt. %.

8. The method according to any one of claim 1, wherein the organic acid is or comprises glyoxylic acid and glycolaldehyde is oxidized into glyoxylic acid according to reaction Scheme 2:

Scheme 2

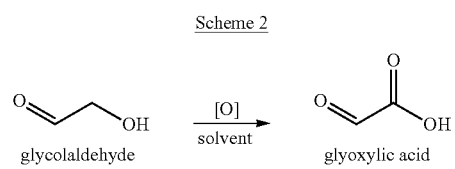

wherein the concentration of nitric acid in the solvent is equal to or lower than 30 wt. %.

9. The method according to claim 8, wherein the selectivity to glyoxylic acid is of at least 45% and the yield to glyoxylic acid is higher than 20%.

10. The method according to claim 8, wherein the concentration of nitric acid in the solvent is from 5 wt. % to 30 wt. %.

11. A mixture comprising glycolaldehyde, nitric acid and a solvent selected from the list consisting of water, ether, methanol and ethanol.

12. The mixture according to claim 11, which further comprises an initiator.

13. The mixture according to claim 12, wherein the initiator is a nitrite salt.

14. The mixture according to claim 13, wherein the nitrite is a nitrite salt selected from the group consisting of ammonium nitrite, sodium nitrite, potassium nitrite, lithium nitrite and mixtures thereof.

* * * * *